United States Patent [19]

Horrobin

[11] Patent Number: 4,996,233
[45] Date of Patent: Feb. 26, 1991

[54] METHOD OF REDUCING PORPHYRIN TOXICITY USING FATTY ACIDS

[75] Inventor: David F. Horrobin, Guildford, England

[73] Assignee: Efamol Limited, Guildford, England

[21] Appl. No.: 480,375

[22] Filed: Feb. 14, 1990

Related U.S. Application Data

[63] Continuation of Ser. No. 903,469, Sep. 4, 1986, abandoned.

[30] Foreign Application Priority Data

Sep. 13, 1985 [GB] United Kingdom ............... 8522670

[51] Int. Cl.$^5$ ...................... A61K 31/20; A61K 31/40
[52] U.S. Cl. .................................. 514/560; 514/886; 514/427
[58] Field of Search .................... 514/560, 886, 427

[56] References Cited

U.S. PATENT DOCUMENTS

| | | | |
|---|---|---|---|
| 2,951,014 | 8/1960 | Garman | 514/152 |
| 3,988,436 | 10/1976 | Loo | 424/59 |
| 4,656,186 | 4/1987 | Bommer et al. | 514/410 |
| 4,681,896 | 7/1987 | Horrobin | 514/552 |
| 4,703,060 | 10/1987 | Traitler et al. | 514/549 |

FOREIGN PATENT DOCUMENTS

| | | | |
|---|---|---|---|
| 3306912 | 1/1985 | Fed. Rep. of Germany | 514/560 |
| 1014956 | 12/1965 | United Kingdom | 514/152 |

OTHER PUBLICATIONS

K. L. Davis et al., *Cholinergic Drugs in Alzheimer's Disease*, Editorials, The New England J. of Med., vol. 315, No. 20, pp. 1286-1287 (1986).

J. H. Growdon et al., *Neurochemical Approaches to the Treatment of Senile Dementia*, Psychopathology in the Aged, pp. 281-294 (1980).

P. Davies, *Theoretical Treatment Possibilities for Dementia of the Alzheimer Type: the Cholinergic Hypythesis*, Theoretical Treatment Strategies for the Development of an Effective Treatment for Senile Dementia, pp. 19-32 (1981).

Martindale, *The Extra Pharmacopoeia*, 28th Ed., (1982), pp. 247, 694-699, and 1217.

*Handbook of Nonprescription Drugs*, 5th Ed. (1977), pp. 282-283.

*The Merck Manual*, 14th Ed. (1982), pp. 313, 952-963 and 2117-2118.

Reyftmann et al., Chem. Abst. 103(7):50054m (1985).

*Primary Examiner*—Douglas W. Robinson
*Assistant Examiner*—Gary E. Hollinden
*Attorney, Agent, or Firm*—Nixon & Vanderhye

[57] ABSTRACT

A method of treating the skin sensitizing effects of porphyrins by the systemic administration of an essential polyunsaturated fatty acid of the N-6 or N-3 series or their metabolites.

2 Claims, No Drawings

METHOD OF REDUCING PORPHYRIN TOXICITY USING FATTY ACIDS

This is a continuation of application Ser. No. 06/903,469, filed Sept. 4, 1986, now abandoned.

FIELD OF THE INVENTION

The invention relates in one aspect to the reduction of undesired skin sensitivity to light in drug treatments and in another aspect to enhancement of the effect of treatment with porphyrins.

GENERAL

Certain drugs increase the sensitivity of the skin to light. Among them are porphyrins, tetracyclines and Benoxaprofen. In particular, porphyrins, used as tumour-locating agents followed by light irradiation to destroy the tumour cells, may require patients to remain in subdued light for some time to avoid generalised skin reactions.

We have found that polyunsaturates, as specified later herein, counter these adverse sensitivities and may be given topically or systemically by ingestion or any other convenient means.

USE OF PORPHYRINS

Haematoporphyrin derivatives of unknown specific composition (HpD, a mixture of tetrapyrroles derived from natural sources) have been used in cancer treatment, having been found to localise in tumours in many tissues after injection into the bloodstream and to sensitise the diseased cells to light irradiation. No explanation for the absorption into tumour cells is known, but irradiated cells (unless pigmented) are rapidly killed to a depth depending on the light penetration. Attention has recently been drawn also to localisation in atheromatous tissue in arteries and also in virus infected cells, giving potential for their selective destruction also.

PRIOR PATENT APPLICATION

In European Patent Application No. 0186962 published July 9, 1986, there are described improvements on HpD in relation to tumour treatment, based on well characterised and thus more exactly controllable compounds.

The published Application discloses when for use in therapy or for the preparation of medicaments therefor, compounds essentially of the formula below. It also discloses methods of therapy, in particular of light-sensitive porphyrin absorbing tumours, making use of the compounds, namely:

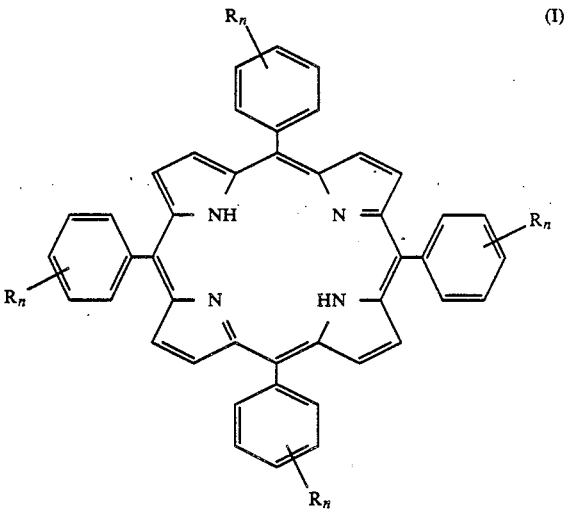

wherein, each R is an ortho, meta or para positioned hydroxy (—OH), amino (—NH$_2$) or suplhhydryl (—SH) substituent optionally itself substituted for example by alkyl or acyl groups preferably C$_1$ to C$_4$. Substitution may be at some or all of the groups R. The R groups and any substituents thereof may be the same or different and in the same or different positions on their respective substitutent rings, which may themselves be replaced by other aromatic ring systems. The nucleus or the substituent rings may be substituted further, provided pharmacological acceptability, appreciable solubility in water, absorption of light at the red end of the spectrum, and absorption by cancerous tissue are retained and the compounds when in such form are to be understood as included in the above formula. Any of the compounds further may be in the form of derivatives such as addition salts at acidic or basic centres, or for example hydrates or other solvates particularly with lower aliphatic alcohols. It is preferred that one or more of the substituents R should be of a kind and in a form able to ionise at physiological pH, to increase the absorption in the red part of the spectrum, that is in the portion that most effectively penetrates tissue.

It is noted further in the published Application that methods of preparation of porphyrin compounds are known in the art and may be used for example to make a preferred compound, itself known, namely 5,10,15,20-tetra(4-hydroxyphenyl)porphyrin (HK7) which may be used as such or as its tetraethyl or tetra-acetyl derivatives. Reference to the published Application shall thus be made for the preparation and properties of the compounds of formula I, and its disclosure is incorporated herein by reference.

Evidence is for example presented (i) that HK7 and other specific compounds are more effective photosensitisers for tumour tissue in animal assay than is HpD and (ii) that they do not cause detectable general cerebral photosensitivity in animals at doses producing substantial tumour sensitisation and, therefore, have promise in the treatment of brain tumours.

PORPHYRIN TREATMENT

In one aspect, the present invention is a development of the use of haematoporphyrins and related compounds, particularly those to which the published Application relates.

On exposure to adequate light intensity, these compounds are raised to an excited state and generate toxic substances such as singlet oxygen and related radicals. These materials thus damage cells which have taken up large amounts of porphyrin. Normal cells do, however, take up the compound and so can be damaged by light exposure. After administration of HpD or related compounds patients must therefore stay in subdued light for a period: otherwise they run the risk of developing severe skin inflammation similar to that which occurs in certain natural porphyrias.

It is thus advantageous to have a method of reducing the damage to normal tissue, which in its present aspect the present invention provides, based on administration of polyunsaturated fatty acids (polyunsaturates) in conjunction with (preferably before, during and after) the administration of the porphyrin and its light activation. Separate administration will normally be convenient but compositions of polyunsaturates and porphyrins are not excluded from the scope of the invention. Administration can be for any indication including cancer, atheroma and inactivation of viruses.

The invention also provides a method of preventing photosensitivity reactions in natural porphyrias in which the porphyrins are endogenously generated.

MODE OF ACTION WITH PORPHYRINS

In addition to protecting normal tissue effectiveness is believed to be related to promotion by polyunsaturates of the formation of superoxide and related radicals, which in cells involved in inflammatory reactions is itself known. By administering the polyunsaturates at a dose level adequate to provide some enrichment of malignant cells, those cells appear to generate toxic radicals more strongly on exposure to porphyrin and light than they would otherwise, with increase in the lethality to those cells of the porphyrin/light treatment of malignancy.

At first sight it is difficult to understand how a polyunsaturate could simultaneously protect normal cells from radiation damage and potentiate that damage in malignant cells. However, it is known that polyunsaturates are vital for the structure of cells and other membranes and for the normal regulation of prostaglandin and leukotriene biosynthesis. These desirable actions must be balanced against possible toxicity resulting from generation of superoxide and other radicals. We have repeatedly observed in cell culture experiments that human malignant cells are damaged by concentrations of polyunsaturated fatty acids which do not damage normal human fibroblasts, suggesting that malignant cells may be less able than normal ones to defend themselves against free radicals and other toxic materials which can be generated from polyunsaturated fatty acids. While we would not wish to be limited by the theory, we suggest that in normal cells the polyunsaturate effect on formation of free radicals and other toxic materials is effectively neutralised, leaving unopposed the important desirable effects of polyunsaturates on cell membranes and other structures, effects which stabilise the cell and reduce light-induced damage. In malignant cells, in contrast, for reasons which are as yet unclear, there appear to be inadequate defences against the polyunsaturate effects of promoting production of free radicals and other toxic substances, so that these toxic effects become predominant and enhance the damage produced by the porphyrin/light interaction.

Broadly therefore the effect of the administration of polyunsaturates prior to, during and after light/porphyrin therapy, is believed to be in potentiating the desired effects of that therapy as well as in reducing the side effects in normal tissues.

DRUGS GENERALLY

The mode of action in reduction of light sensitivity of the skin in use of the other drugs, such as tetracyclines, and of normal tissue in use of porphyrins, is less clear but may be due to an effect of these drugs in disturbing the normal bodily function of polyunsaturates reducing their effects so that supplementation is required.

THE INVENTION

The invention thus lies in drug treatments using the drugs referred to in conjunction with polyunsaturates. The invention lies also in compositions of the drugs and the polyunsaturates, for use where convenient, and in preparation of medicaments, being such compositions for such purpose.

DOSES 1 mg to 500 g per day of the polyunsaturates, preferably 100 mg to 10 g, or molar equivalent amounts of derivatives as referred to below. The polyunsaturates can be administered for days, weeks or even months prior to the drug, particularly light/porphyrin, treatment and continued for similar periods afterwards depending on the retention of the drug in the body (elimination of porphyrins is slow). The drug treatment is itself conventional.

Dosages with the porphyrins of the published Application require a balance between doses being high enough to show useful necrosis and not so high as to be prohibitively toxic. For example, the lithium, sodium and zinc salts of HK7 show useful necrosis at 12.5 $\mu$m/kg, $\mu$m/kg=micromols, while HK7 itself is reasonably effective at 6.25 $\mu$m/kg. We would expect the most effective does in man to lie in the range of 0.25-1.0 mg/kg subject to the fact that the safe and effective range for a given compound must be found by trial. At its widest, subject always to that proviso, the range will not be outside 0.01 to 10.0 (or possibly up to 100) mg/kg. Ranges for the dose of illumination are, for example, 2.5 to 500 J/cm$^2$ conveniently 5 to 250 J/cm$^2$ depending primarily on tumour thickness. In some instances more than one such does of light may be desirable following a single, or possibly, more than one such administration of the porphyrin.

SUITABLE POLYUNSATURATES

The polyunsaturates used are preferably the essential fatty acids of the n-6 and n-3 series.

The pathways of metabolism of the n-6 essential fatty acids and the related n-3 acids sharing, it is believed, common enzymes in the two pathways, are:

| n-6 | | n-3 | |
|---|---|---|---|
| 18:2 | delta-9,12 (linoleic acid) | 18:3 | delta-9,12,15 (alpha-linolenic acid) |
| ↓ | delta-6 desaturase | ↓ | |
| 18:3 | delta-6,9,12 (gamma-linolenic acid) | 18:4 | delta 6,9,12,15 |
| ↓ | elongation | ↓ | |
| 20:3 | delta-8,11,14 (dihomo-gamma-linolenic acid) | 20:4 | delta-8,11,14,17 |
| ↓ | delta-5 desaturase | ↓ | |

-continued

| n-6 | | n-3 | |
|---|---|---|---|
| 20:4 | delta-5,8,11,14 (arachidonic acid) | 20:5 | delta-5,8,11,14,17 |
| ↓ | elongation | ↓ | |
| 22:4 | delta-7,10,13,16 (adrenic acid) | 22:5 | delta-7,10,13,16,19 |
| ↓ | delta-4 desaturase | ↓ | |
| 22:5 | delta-4,7,10,13,16 | 22:6 | delta-4,7,10,13,16,19 |

The pathways are not normally reversible nor, in man, are n-3 and n-6 series acids interconvertible.

The acids, which naturally are of the all-cis configuration, are systematically named as derivatives of the corresponding octadecanoic, eicosanoic or docosanoic acids, e.g. delta-9,12-octadecadienoic acid or delta-4,7,10,13,16,19-docosahexaenoic acid, but numerical designation such as, correspondingly, 18:2 n-6 or 22:6 n-3 is convenient. Initials, for example DHA for 22:6 n-3 (docosahexaenoic acid), are also used but do not serve when n-3 and n-6 acids of the same chain length and degree of unsaturation exist. Trivial names in more or less common use in the n-6 series are as shown. Of the n-3 series only 18:3 n-3 has a commonly used trivial name, alpha-linolenic acid. It was characterised earlier than gamma-linolenic acid and reference in the literature simply to linolenic acid, especially in the earlier literature is to the alpha-acid.

The acids may be used as such or as pharmaceutically acceptable and physiologically equivalent derivatives as, for example, detailed later herein for gamma-linolenic acid and dihomo-gamma-linolenic acid, and reference to any of the acids is to be taken as including reference to the acids when in the form of such derivatives. Equivalence is demonstrated by entry into the pathways quoted herein, as evidenced by effects corresponding to those of the acids themselves or their natural glyceride esters. Thus, indirect identification of useful derivatives is by their having the valuable effect in the body of the acid itself, but conversion can be shown directly by gas chromatographic analysis of concentrations in blood, body fat, or other tissue by standard techniques, for example those of Pelick et al. p. 23, "Analysis of Lipids and Lipoproteins" Ed. Perkins, American Oil Chemist Society, Champaign, Ill., U.S.A.

PACKS

If it is not desired to have compositions comprising the different active materials together, packs may be prepared comprising the materials presented for separate, or part joint and part separate administration in the appropriate relative amounts, and use of such packs is within the purview of this invention.

FORMS AND SOURCES OF GAMMA-LINOLENIC AND OTHER ACIDS

Convenient physiologically equivalent derivatives of gamma-linolenic acid and dihomo-gamma-linolenic acid for use according to the invention, as with the other acids, include salts, amides, esters including glyceride esters and alkyl (e.g. $C_1$ to $C_4$) esters, and phospholipids. As noted above, reference to the acids in the claims and elsewhere herein are to be taken as including them when in the form of said derivatives.

If desired, pharmaceutical compositions may be produced for use in the invention by associating the natural or synthetic acids, as such or as derivatives, with an acceptable pharmaceutical vehicle. It is, however, at present convenient to incorporate at least the gamma-linolenic acid into compositions in the form of an available oil having a high gamma-linolenic acid content, hence reference to "oil" herein.

At the present time known natural sources of oils having a high gamma-linolenic acid content are few (there are no known natural sources of significant amounts of dihomo-gamma-linolenic acid). One source of oils currently available is the seed of Evening Primrose species such as *Oenothera biennis L.* and *Oenothera lamarckiana,* the oil extract therefrom containing gamma-linolenic acid (about 8%) and linoleic acid (about 72%) in the form of their glycerides together with other glycerides (percentages based on total fatty acids). Other sources of gamma-linolenic acid are Borage species such as *Borago officinalis* which, though current yield per acre is low, provide a richer source of gamma-linolenic acid than Oenothera oil. Recent studies on fungi which can be cultivated by fermentation promise a fungal oil source.

The oil is extracted from the seed by one of the conventional methods of extraction such as cold pressure, screw pressure after partially cooking the seed, or solvent extraction.

Fractionation of a typical sample of this oil in the form of methyl esters shows the relative proportions:

| | |
|---|---|
| Palmitate | 6.15 |
| Stearate | 1.6 |
| Oleate | 10.15 |
| Linoleate | 72.6 |
| Gamma-linolenate | 8.9 |

The seed oil extracts referred to above can be used as such or can, for example, if desired, be fractionated to yield an oily composition containing the triglycerides of gamma-linolenic and linoleic as the main fatty acid components, the gamma-linolenic acid content being if desired a major proportion. Seed oil extracts appear to have a stabilising effect upon dihomo-gamma-linolenic acid if present.

Natural sources of 22:4 and 22:5 n-6 acids include adrenal glands (22:5) and kidneys (22:4) obtained from slaughter houses, and 22:4 in the fat of the American Snapping Turtle. The n-3 acids are available from fish oils, particularly 20:5 n-3 and 22:6 n-3.

The acids can be isolated from these sources by, for example, saponification under mild non-oxidising conditions followed by preparative gas liquid chromatography. Synthesis of the acids is difficult but not impossible and provides another source.

Advantageously, a preservative is incorporated into the preparations: alpha-tocopherol in conenctration of about 0.1% by weight has been found suitable for the purpose.

EXAMPLES

Soft gelatine capsules made by conventional methods are administered in conjunction with tetracycline, Benoxaprofen, HpD or KH7 treatment in doses conventional for such treatment or in the case of treatment with HK7 daily doses as set out in the published Application, in the preferred range of 0.25–1.0 mg/kg, as follows:

1. 500 mg capsules of Evening Primrose Oil containing 45 mg gamma-linolenic acid, 6/day;

2. 500 mg capsules of borage oil containing 90 mg gamma-linolenic acid, 4/day;
3. 100 mg capsules of pure gamma-linolenic acid, 4/day;
4. 50 mg capsules of pure dihomo-gamma-linolenic acid, 6/day;
5. Capsules containing 100 mg gamma-linolenic acid, 20 mg 20:4 n-6, 50 mg 20:5 n-3, 5/day;
6. Capsules containing 100 mg gamma-linolenic acid, 50 mg 22:4 n-6, 50 mg 20:5 n-3, 50 mg 22:6 n-3, 5/day.

A pack as referred to herein comprises 500 mg capsules of Evening Primrose Oil as above, to be taken 6/day, together, for example, with HpD or HK7 treatment.

Treatment with HK7 may, for example, specifically be:

1. Administer, for 14 days prior to injection of the porphyrin, 8 capsules per day of 80% Evening Primrose Oil and 20% fish oil (as a source of 20:5 and 22:6 n-3 acids);
2. Administer the porphyrin at 12.5 μm/kg and after the appropriate interval expose the tissue to laser irradiation while continuing the administration of the polyunsaturates;
3. Continue administration of the polyunsaturates for 8 weeks after laser irradiation.

I claim:

1. A method of reducing the skin-sensitizing effects of porphyrins administered therapeutically, said method comprising systemically administering to a person to whom porphyrins are being therapeutically administered from 1 mg to 500 g of a polyunsaturated fatty acid of the n-6 series or its metabolites and an essential fatty acid of the n-3 series or its metabolites, alone or in an acceptable pharmaceutical diluent or carrier.

2. A method of reducing the skin sensitizing effects of porphyrins administered therapeutically, said method comprising systemically administering to a person to whom porphyrins are being therapeutically administered from 1 mg to 500 g of a polyunsatirated fatty acid selected from the group consisting essentially of an essential fatty acid of the n-6 series and an essential fatty acid of the n-3 series, alone or in an acceptable pharmaceutical diluent or carrier.

* * * * *